United States Patent
Muthusamy et al.

(10) Patent No.: US 10,519,086 B2
(45) Date of Patent: Dec. 31, 2019

(54) MAGNETIC SEPARATION AND RECYCLE OF CATALYST COMPONENTS IN A BIO-MASS TO GLYCOLS PROCESS

(71) Applicant: SHELL OIL COMPANY, Houston, TX (US)

(72) Inventors: Duraisamy Muthusamy, Houston, TX (US); Viet Quoc Nguyen, Houston, TX (US)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 16/328,085

(22) PCT Filed: Aug. 30, 2017

(86) PCT No.: PCT/US2017/049270
§ 371 (c)(1),
(2) Date: Feb. 25, 2019

(87) PCT Pub. No.: WO2018/044971
PCT Pub. Date: Mar. 8, 2018

(65) Prior Publication Data
US 2019/0185398 A1 Jun. 20, 2019

Related U.S. Application Data

(60) Provisional application No. 62/381,084, filed on Aug. 30, 2016.

(51) Int. Cl.
| | |
|---|---|
| *C07C 29/76* | (2006.01) |
| *B01J 23/00* | (2006.01) |
| *B01J 25/00* | (2006.01) |
| *B01J 23/30* | (2006.01) |
| *B01J 25/04* | (2006.01) |
| *B01J 35/00* | (2006.01) |
| *B01J 38/72* | (2006.01) |
| *C07C 29/141* | (2006.01) |
| *C07C 31/20* | (2006.01) |

(52) U.S. Cl.
CPC ............... *C07C 29/76* (2013.01); *B01J 23/30* (2013.01); *B01J 25/04* (2013.01); *B01J 35/006* (2013.01); *B01J 35/0033* (2013.01); *B01J 38/72* (2013.01); *C07C 29/141* (2013.01); *C07C 31/202* (2013.01)

(58) Field of Classification Search
CPC ........ C07C 29/76; C07C 29/141; B01J 23/30; B01J 25/04
See application file for complete search history.

(56) References Cited

FOREIGN PATENT DOCUMENTS

WO   2016114661 A1   7/2016

OTHER PUBLICATIONS

International Search Report and Written Opinion received for PCT Patent Application No. PCT/US2017/049270, dated Dec. 4, 2017, 9 pages.
Ye et al., "Improved Performance of Magnetically Recoverable Ce-promoted Ni/Al2O3 catalysts for Aqueous-phase Hydrogenolysis of Sorbitol to Glycols", Catalysis Today, vol. 183, Issue No. 1, Aug. 31, 2011, pp. 65-71, XP028902804.

*Primary Examiner* — Sikarl A Witherspoon

(57) ABSTRACT

Implementations of the disclosed subject matter provide a process for producing ethylene glycol from a carbohydrate feed. The process may include contacting, in a reactor under hydrogenation conditions, the carbohydrate feed with a bi-functional catalyst system which may include a heterogeneous hydrogenation catalyst including a magnetically active metal, and a soluble retro-Aldol catalyst including tungstate. A liquid effluent stream may be obtained from the reactor and may include hydrogenation catalyst particles and tungsten oxide precipitate particles. The hydrogenation catalyst particles may be magnetically separated from the tungsten oxide precipitate particles in the liquid effluent stream using a magnet in a separation vessel. The separated hydrogenation catalyst particles may be retained in a separation zone in the separation vessel and may be subsequently removed from the separation zone. A liquid product stream may be obtained from the separation vessel and may include the tungsten oxide precipitate particles and ethylene glycol.

10 Claims, 3 Drawing Sheets

MAGNETIC SEPARATION AND RECYCLE OF CATALYST COMPONENTS IN A BIO-MASS TO GLYCOLS PROCESS

CROSS REFERENCE TO RELATED APPLICATIONS

This is a national stage application of International Application No. PCT/US2017/049270, filed 30 Aug. 2017, which claims benefit of priority to U.S. Provisional Application No. 62/381,084, filed 30 Aug. 2016.

TECHNICAL FIELD OF THE INVENTION

The presently disclosed subject matter relates to a process for preparing glycols, particularly ethylene glycol and propylene glycol, by converting a carbohydrate feed stock material in a reactor using a bi-functional catalyst system. More specifically, the presently disclosed subject matter relates to a process for magnetically separating and subsequently recycling catalyst components in a process for preparing glycols.

BACKGROUND

Glycols such as ethylene glycol and propylene glycol are valuable materials with a multitude of commercial applications, e.g. as heat transfer media, antifreeze, and precursors to polymers, such as PET. The market for ethylene and propylene glycols (EG and PG) is expanding worldwide, with the EG market being vastly bigger than the market for PG (i.e., 1,2-propylene glycol). Ethylene and propylene glycols are typically made on an industrial scale by hydrolysis of the corresponding alkylene oxides, which are the oxidation products of ethylene and propylene, produced from fossil fuels/petrochemical feed stocks involving multiple processing steps. Use of bio-based feed stocks for the production of energy and chemicals has become increasingly desirable in the industry since this approach to use feeds from renewable sources provides a pathway for sustainable development.

In recent years, increased efforts have focused on producing chemicals, including glycols, from renewable feedstocks, such as carbohydrate-containing feedstock. Carbohydrates are plentiful and renewable bio-mass feeds having the structural features resembling that of ethylene glycol; each carbon has one attached hydroxyl group or contains an oxygen function that can be readily converted into a hydroxyl. As such, EG and PG can be produced if the C—C bonds are selectively cleaved into $C_2$ and $C_3$ units.

As with many chemical processes, the reaction product stream in these processes comprises a number of desired materials as well as diluents, by-products and other undesirable materials. In order to provide a high value process, the desirable product or products must be obtainable from the reaction product stream in high purity with a high percentage recovery of each product and with as low as possible use of energy, chemical components and complex equipment.

Therefore, it would be advantageous to provide an improved method suitable for separation, regeneration, and recycle of catalyst components in the production of glycols from carbohydrate feeds in order to make the overall glycol production process more economical than processes disclosed previously in the industry.

BRIEF SUMMARY

Implementations of the disclosed subject matter provide a process for producing ethylene glycol from a carbohydrate feed. The process may include contacting, in a reactor under hydrogenation conditions, the carbohydrate feed with a bi-functional catalyst system which may include a heterogeneous hydrogenation catalyst including a magnetically active metal, and a soluble retro-Aldol catalyst including tungstate. A liquid effluent stream may be obtained from the reactor and may include hydrogenation catalyst particles and tungsten oxide precipitate particles. The hydrogenation catalyst particles may be magnetically separated from the tungsten oxide precipitate particles in the liquid effluent stream using a magnet in a separation vessel. The separated hydrogenation catalyst particles may be retained in a separation zone in the separation vessel and may be subsequently removed from the separation zone. A liquid product stream may be obtained from the separation vessel and may include the tungsten oxide precipitate particles and ethylene glycol.

Implementations of the disclosed subject matter provide an improved method for producing ethylene glycol from a carbohydrate feed. The disclosed subject matter allows for magnetic separation of catalyst components for subsequent recycle in the process for producing glycols. An advantage of the disclosed magnetic separation and recycle technique is that it provides a solution to the problem of separating the oxides of tungsten from the hydrogenation catalyst, both of which are present in the reactor as small particles. Another advantage of the disclosed magnetic separation and recycle technique is that it allows for the production of the desirable products of EG and PG in high yields and high percentage recovery with a relatively low use of energy, chemical components and complex equipment as compared to prior art processes. The disclosed method results in a production of glycols from carbohydrate feeds that makes the overall glycol production process more economical than processes disclosed previously in the industry.

Additional features, advantages, and embodiments of the disclosed subject matter may be set forth or apparent from consideration of the following detailed description, drawings, and claims. Moreover, it is to be understood that both the foregoing summary and the following detailed description are examples and are intended to provide further explanation without limiting the scope of the claims.

BRIEF DESCRIPTION OF THE DRAWINGS

The accompanying drawings, which are included to provide a further understanding of the disclosed subject matter, are incorporated in and constitute a part of this specification. The drawings also illustrate embodiments of the disclosed subject matter and together with the detailed description serve to explain the principles of embodiments of the disclosed subject matter. No attempt is made to show structural details in more detail than may be necessary for a fundamental understanding of the disclosed subject matter and various ways in which it may be practiced.

DETAILED DESCRIPTION

Figure 1:
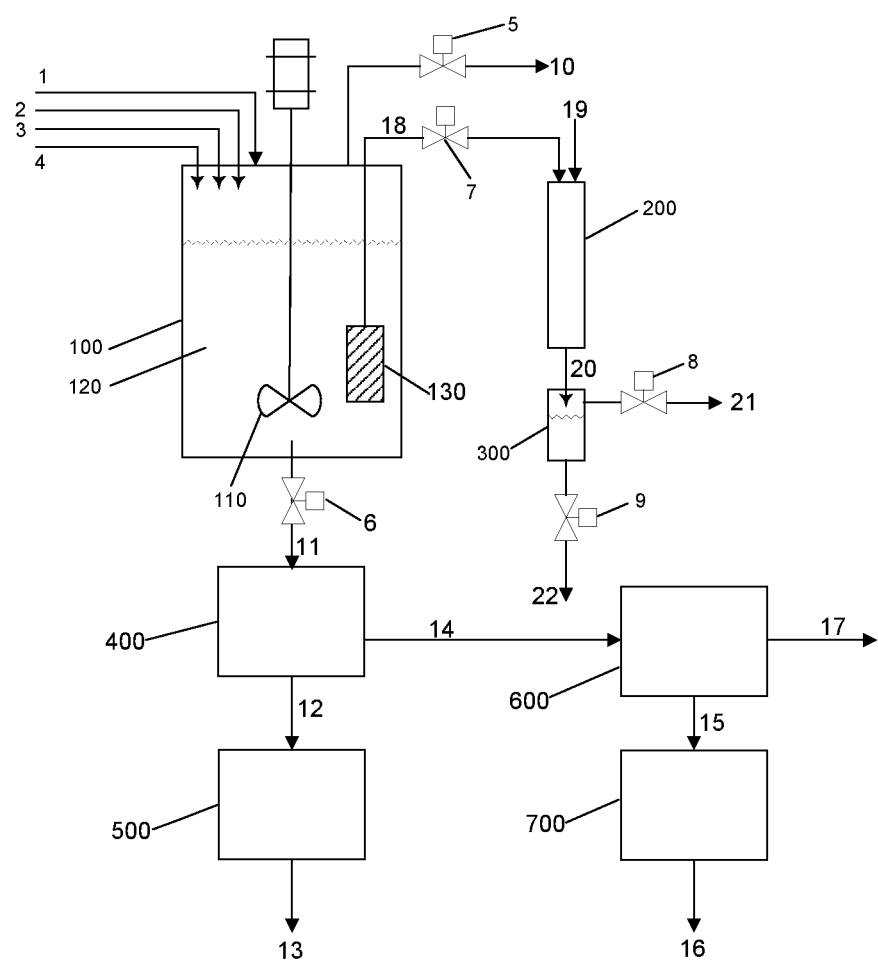
FIG. 1 shows an example process scheme according to an implementation of the disclosed subject matter.

Carbohydrates are readily available and renewable bio-mass feeds, and they have the structural features resembling that of ethylene glycol; each carbon has one attached hydroxyl group or contains an oxygen function that can be readily converted into a hydroxyl. Ethylene glycol (EG) and propylene glycol (PG) can be produced by selectively cleaving the C—C bonds into $C_2$ and $C_3$ units. As such, the presently disclosed subject matter provides a process for the conversion of carbohydrate feed stock materials and hydrogen gas into glycols, particularly with ethylene glycol as the main product and propylene glycol as a smaller co-product.

The process variables have major impacts on the conversion and selectivity of the reaction. For example, the particular catalyst(s) used and process conditions can provide for a successful reaction selectivity outcome under a set of practical reaction conditions. In addition, the ability to separate, regenerate, and recycle catalyst components are important to the overall success of the bio-mass to glycols process and the ability to operate the reactor in an uninterrupted continuous mode.

The sugars to glycols hydrogenolysis reaction, which is carried out using a metal catalyst and in the presence of hydrogen, is a complex reaction known to produce hundreds of products. Since ethylene and propylene glycols are the desired products, the other products must be minimized by selecting the appropriate catalyst and conditions; additionally an EG/PG wt % ratio of at least 1:1 and preferably 7:1 or more is desirable. In general, sugars tend to cleave into $C_3$ fragments more easily than the desired $C_2$ fragment, resulting in the formation of propylene glycol as the single most predominant molecule. While the selection of the most appropriate catalyst, not only from the selectivity point of view but also from the point of view of catalyst longevity, is an important task, other aspects of the reaction must also be considered. The catalyst generally only controls the chemistry taking place on its surface; for example, the cleavage of the sugar molecules into smaller fragments taking place by discrete retro-Aldol reactions followed by hydrogenation of the intermediates into products is the desired pathway. However, quite a number of other reactions take place in solution and these side reactions must also be considered. A number of ions such as OH−, OAc−, etc. could be present in the solution under basic pH conditions or H+ ions could be present under acidic pH conditions. While these ions could also catalyze the retro-Aldol reaction, these ions are generally known to catalyze a variety of dehydration side-reactions causing the sugar molecules to degrade into wasteful products. These undesirable side reactions could become dominant particularly under high temperature conditions. A proper choice of catalysts and process conditions is therefore essential in order to realize the objectives of high glycol yields and long catalyst life. Multiple equations can be used to explain the various steps of the chemistry of the conversion of sugars to EG and PG, as shown below.

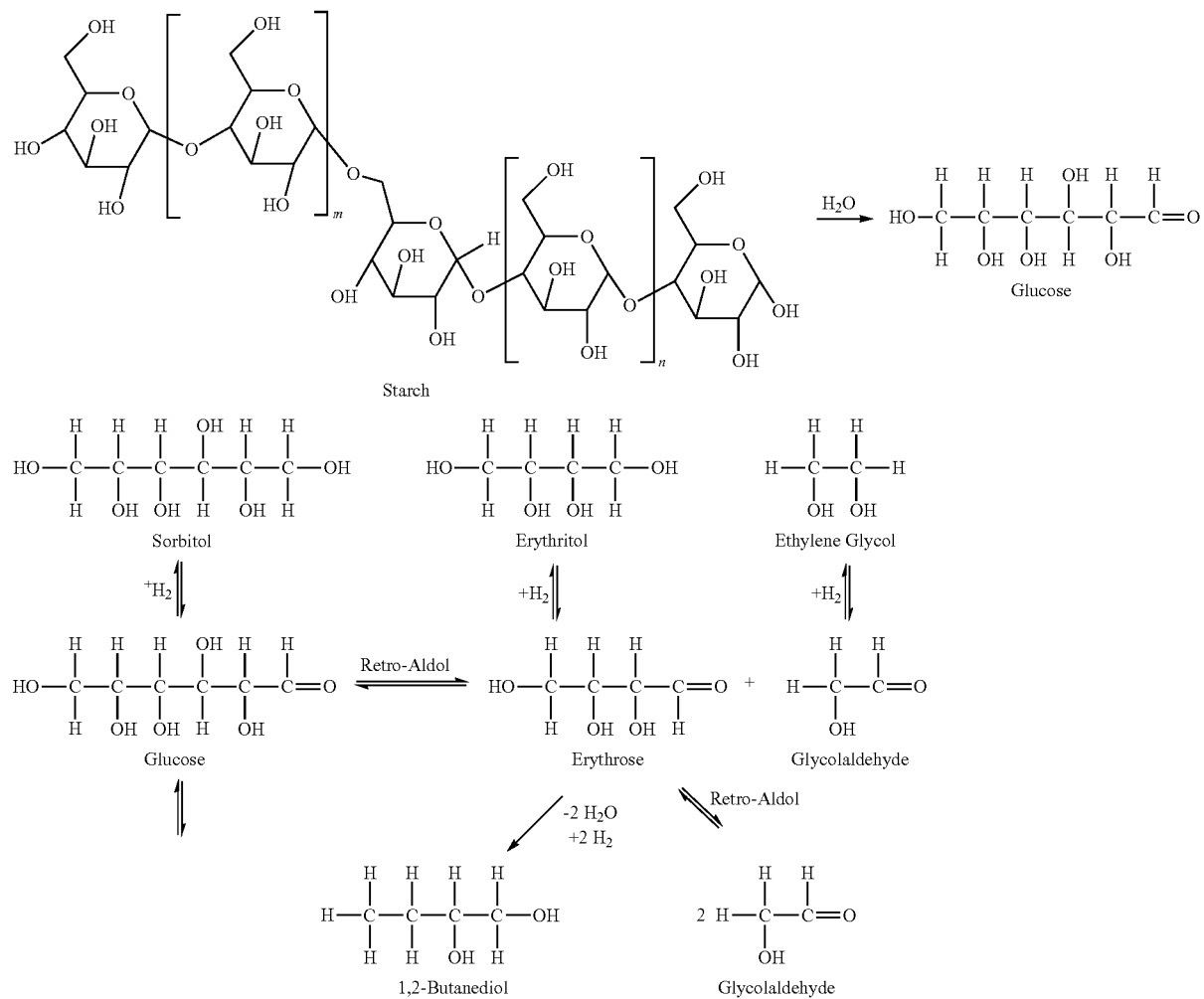

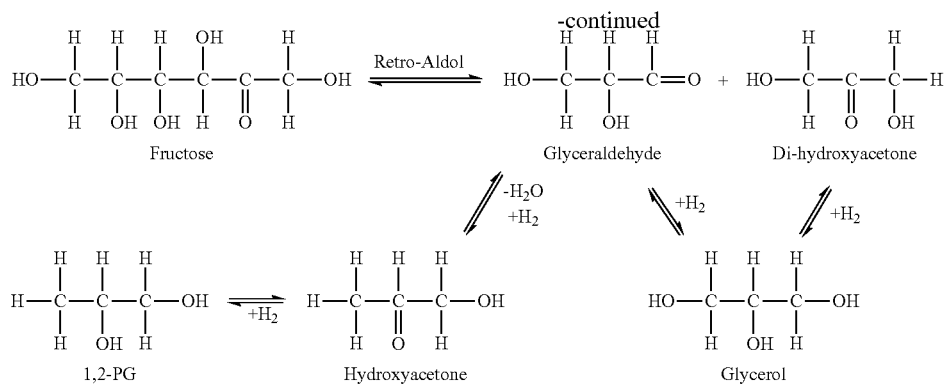

As shown above, the chemistry of sugars in the hydrogenolysis reaction is a notoriously complex set of functional group chemistries; the products from any reaction could be reactants for all other reactions, including those taking place on the surface of the solid catalyst. The product distribution (EG, PG, partially converted sugars, etc.) at the end of reaction will be a function of the relative rates of these reactions under the chosen experimental conditions. Thus, according to the presently disclosed subject matter, a technique for separating and recycling the catalyst components has been determined for the disclosed method for producing ethylene glycol from a carbohydrate feed.

The presently disclosed method for producing ethylene glycol from a carbohydrate feed has numerous advantages over the prior art. The disclosed method provides for a separation technique allows for superior results in terms of product yield, catalyst stability, and extended run time (e.g., suitable for commercialization). The presently disclosed method also allows for an efficient use of the catalyst materials and minimizes the generation of waste catalyst materials in the glycols production process, thus resulting in improved economics and environmental benefits.

According to an implementation of the disclosed subject matter, the process may include contacting, in a reactor under hydrogenation conditions, the carbohydrate feed with a bi-functional catalyst system which may include a heterogeneous hydrogenation catalyst including a magnetically active metal, and a soluble retro-Aldol catalyst including tungstate. A liquid effluent stream may be obtained from the reactor and may include hydrogenation catalyst particles and tungsten oxide precipitate particles. The hydrogenation catalyst particles may be magnetically separated from the tungsten oxide precipitate particles in the liquid effluent stream using a magnet in a separation vessel. The separated hydrogenation catalyst particles may be retained in a separation zone in the separation vessel and may be subsequently removed from the separation zone. A liquid product stream may be obtained from the separation vessel and may include the tungsten oxide precipitate particles and ethylene glycol.

According to an embodiment, a carbohydrate feed may include one or more of glucose, sucrose, xylose, sugar cane molasses, starch, and cellulose. Suitable reactor vessels to be used in the process of the preparation of ethylene glycol from a carbohydrate feed include continuous stirred tank reactors (CSTR), plug-flow reactors, slurry reactors, ebbulated bed reactors, jet flow reactors, mechanically agitated reactors, back-mixed reactors, bubble columns, such as slurry bubble columns and external recycle loop reactors. The use of these reactor vessels allows dilution of the reaction mixture to an extent that provides high degrees of selectivity to the desired glycol product (mainly ethylene and propylene glycols). There may be one or more of such reactor vessels, arranged in series. In one embodiment, preferably there are two reactor vessels arranged in series, the first one of which is a CSTR, the output of which is supplied into a plug-flow reactor.

The disclosed method for producing ethylene glycol from a carbohydrate feed may be performed under particular hydrogenation conditions in order to maximize the desired yield of EG. For example, the hydrogenation conditions may include temperature, pressure, flow rate, and any other process variable that may be controlled. In an embodiment, the hydrogenation conditions may include a temperature in the range of from 180-250° C. and from 210-250° C. The hydrogenation conditions may also include a pressure in the range of from 500 to 2000 psig.

In an embodiment, the presently disclosed method may also include contacting the carbohydrate feed with hydrogen. For example, the disclosed method may take place in the presence of hydrogen. Hydrogen may be supplied into the reactor vessel under pressure in a manner common in the art. Hydrogen is supplied into the reactor vessels under pressure. In an example, the method of the present reaction takes place in the absence of air or oxygen. In order to achieve this, it is preferable that the atmosphere in the reactor vessel be evacuated and replaced with hydrogen repeatedly, after loading of any initial reactor vessel contents, before the reaction starts.

According to an embodiment, the bi-functional catalyst system may include a heterogeneous hydrogenation catalyst comprising a magnetically active metal, and a soluble retro-Aldol catalyst comprising tungstate. The heterogeneous hydrogenation catalyst may comprise one or more materials selected from transition metals from groups 8, 9, 10, 11 or compounds thereof, with catalytic hydrogenation capabilities. The heterogeneous hydrogenation catalyst may comprise one or more of iron, cobalt, nickel, ruthenium, rhodium, palladium, iridium and platinum. The heterogeneous hydrogenation catalyst may include at least one magnetically active metal selected from nickel, cobalt, iron, rare earth metals, and combinations thereof. This heterogeneous hydrogenation catalyst may be present in the elemental form or as a compound. It may also be suitable that this heterogeneous hydrogenation catalyst is present in chemical combination with one or more other ingredients in the catalyst system. In an embodiment, the heterogeneous hydrogenation catalyst may be a Raney-type catalyst. According to an embodiment, the heterogeneous hydrogenation catalyst may comprise at least one of Raney-Ni, Raney-Co, Raney-Cu, Raney-Ru, Cu, Co, and Ru. According to an implementation, the heterogeneous hydrogenation catalyst may be a nano-particle metal comprising any metal selected from Groups 8, 9, 10, or 11. In some cases, the heterogeneous hydrogenation catalyst may be further promoted with one or more metals such as Fe, Cr, Mn, Mo, W, Re, Rh, Pd, Ag, Au, Pt, Ir, and La. In an embodiment, the heterogeneous hydrogenation catalyst may be provided in sulfided form.

In an embodiment, the tungstate in the soluble retro-Aldol catalyst may be at least one of sodium meta-tungstate, ammonium meta-tungstate, ammonium tungstate, sodium poly-tungstate, tungstic acid, alkali- and alkaline-earth metal tungstates, sodium phospho-tungstate, phospho-tungstic acid, alkali- and alkaline-earth metal phospho-tungstates, alkali- and alkaline-earth metal molybdates, alkali- and alkaline-earth metal phospho-molybdates, phospho-molybdic acid, heteropoly acids, mixed tungstates and molybdates, niobic acid, silicotungstic acid, alkali-alkaline-earth metal niobates, and combinations thereof.

According to an embodiment, at least one of the heterogeneous hydrogenation catalyst and soluble retro-Aldol catalyst of the bi-functional catalyst system is supported on a solid support. In an embodiment, any other active catalyst component may be present in either heterogeneous or homogeneous form. In this case, any other active catalyst component may also be supported on a solid support. In one embodiment, the heterogeneous hydrogenation catalyst is supported on one solid support and the soluble retro-Aldol catalyst is supported on a second solid support which may comprise the same or different material. As a specific example, the heterogeneous hydrogenation catalyst may be a hydrogenation catalyst supported on a hydrothermally stable support. In another embodiment, both the heterogeneous hydrogenation catalyst and soluble retro-Aldol catalyst are supported on one solid hydrothermally stable support.

The solid support may be in the form of a powder or in the form of regular or irregular shapes such as spheres, extrudates, pills, pellets, tablets, monolithic structures. Alternatively, the solid supports may be present as surface coatings, for examples on the surfaces of tubes or heat exchangers. Suitable solid support materials are those known to the skilled person and include, but are not limited to aluminas, silicas, zirconium oxide, magnesium oxide, zinc oxide, titanium oxide, carbon, activated carbon, zeolites, clays, silica alumina and mixtures thereof.

According to the presently disclosed subject matter, a liquid effluent stream may be obtained from the reactor. This liquid effluent stream may include hydrogenation catalyst particles and tungsten oxide precipitate particles. The solid particles may accumulate in the reactor, and thus require to be removed from the reactor and separated from one another.

In an embodiment according to step (c), the hydrogenation catalyst particles may be magnetically separated from the tungsten oxide precipitate particles in the liquid effluent stream using a magnet in a separation vessel. The magnet used in step (c) may be selected based on at least one property including magnetic power of the magnet, particle size of the hydrogenation catalyst particles, velocity of the liquid effluent from the reactor, and the magnetic power of the magnetically active metal of the hydrogenation catalyst. As an example, the magnet used in step (c) may be selected to optimize the magnetic separation power and/or magnetic attraction of the hydrogenation catalyst particles in order to achieve the desired separation. The separated hydrogenation catalyst particles may be retained in a separation zone in the separation vessel.

A separation vessel may be any vessel useful for magnetically separating and retaining the hydrogenation catalyst particles. For example, the separation vessel may be the reactor used for the process or a portion of the reactor used for the process. In an embodiment, the separation vessel may be a drum separator such as a rotating drum magnet separator.

The separated hydrogenation catalyst particles may be removed from the separation zone of the separation vessel in step (d). Removal of the separated hydrogenation catalyst particles may be achieved a variety of ways. For example, the separated hydrogenation catalyst particles may be continuously removed from the separation zone of the separation vessel. In another example, the separated hydrogenation catalyst particles may be periodically removed using a filter. Further details on these various examples of separation schemes are provided below with reference to FIGS. 1-3. Following magnetic separation, the separated hydrogenation catalyst particles from step (d) may be combined with at least a portion of the liquid product stream to form a slurry that is recycled back to the reactor in step (a) for further processing. According to the presently disclosed subject matter, the ability to recycle the separated hydrogenation catalyst particles allows for the operation of the reactor in an uninterrupted continuous mode and also facilitates the complete recycle of the retro-Aldol catalyst.

In an embodiment according to step (e), a liquid product stream may be obtained from the separation vessel. This liquid product stream may include the tungsten oxide precipitate particles and ethylene glycol. According to an embodiment, the process may also include separating the tungsten oxide precipitate particles from the liquid product stream to produce an intermediate product stream free of both the hydrogenation catalyst particles and the tungsten oxide precipitate particles.

FIG. 1 shows an example process scheme according to an implementation of the disclosed subject matter. As shown in FIG. 1, an apparatus and scheme used to perform the conversion of carbohydrate feeds into glycols using a catalyst system comprising a heterogeneous hydrogenation catalyst and a homogeneous tungstate retro-Aldol catalyst, and recovery and magnetic separation of the catalyst components are schematically represented. Reactor 100 may be equipped with stirrer 110 and catalyst filter 130. The reactor may also be equipped with automatic controls for the control of reactor temperature, back-pressure, liquid holdup level, stirrer speed, etc. The feed line 1 may be equipped with a gas flowmeter and may be used to provide a continuous flow of hydrogen gas into the reactor. Each of the feed lines 2 to 4, may be used to send liquid or slurry streams into the reactor, and may be equipped with a pump and a mass flow meter. These lines 2-4 may be used to continuously add the carbohydrate feed (e.g., glucose solution or slurry of starch in water), solution of sodium meta-tungstate retro-Aldol catalyst, and optionally an alcoholic solvent to the reactor 100. Optionally, the carbohydrate feed and the tungstate retro-Aldol catalyst may be combined as a single liquid feed stream. Normally, the heterogeneous hydrogenation catalyst is charged to the reactor 100 at the beginning of the reactor operation. Optionally, one of the feed lines 2 to 4 can be converted for a continuous addition of the heterogeneous hydrogenation catalyst. The filter 130 may be used to retain the heterogeneous hydrogenation catalyst and the precipitated oxides of tungsten (W-oxides) present in the reaction medium 120 while allowing the flow of the liquid product via line 18. The flow of the product stream may be controlled by valve 7. The excess gas present in the reactor 100 may be vented by the use of the back-pressure control valve 5. The vent gas may be vented via stream 10.

Reactor 200 may be a tubular reactor containing a catalyst section in the middle and may be used to complete the hydrogenation of the product. This reactor 200 may be equipped with heater temperature controls and inside thermocouples for measuring the temperature of the catalyst bed. The gas feed line 19 may be equipped with a flowmeter and it may be used to continuously feed hydrogen to reactor 200. Line 20 may be an in-line product cooler to cool down the product mixture. The gas-liquid product effluent passing through line 20 may be set up to flow into a gas/liquid separator vessel 300. Valve 8 may be used to control the back-pressure in vessel 300 and valve 9 may be used to control the liquid level in the vessel. The vent gas may be vented via stream 21 and the product may be obtained via stream 22.

In the operation of reactor 100, valve 6 may be kept closed and the product stream 22 may be continuously produced. When the activity of the catalyst system retained inside the reactor has declined to unacceptable levels, the feeds may be stopped and the reactor contents, which include the magnetically active heterogeneous hydrogenation catalyst and the precipitated oxides of the retro-Aldol catalyst, may be removed from reactor 100 by opening valve 6 and sent to vessel 400 via line 11. The magnetic separation of the hydrogenation catalyst particles may be carried out in vessel 400. The magnetically active particles of the hydrogenation catalyst, Raney® nickel in this example case, may be sent to the storage vessel 500 via line 12. The hydrogenation catalyst may be removed from vessel 500 via line 13 for further conditioning or a direct recycle back into the glycols production in reactor 100.

The liquid stream resulting from the magnetic separation in vessel 400, still containing the suspended particles of the W-oxides, may be passed to vessel 600 via line 14. The solids may be separated from the liquid in vessel 600, removed via line 15, and sent to storage vessel 700. The solids may be removed from vessel 700, via line 16, for a catalyst reactivation step before recycling to the glycols production in reactor 100. The liquid stream 17 leaving vessel 700 is a small portion of the overall product produced in reactor 100 and may be combined with the main product stream 22 or optionally passed through reactor 200.

Figure 2:
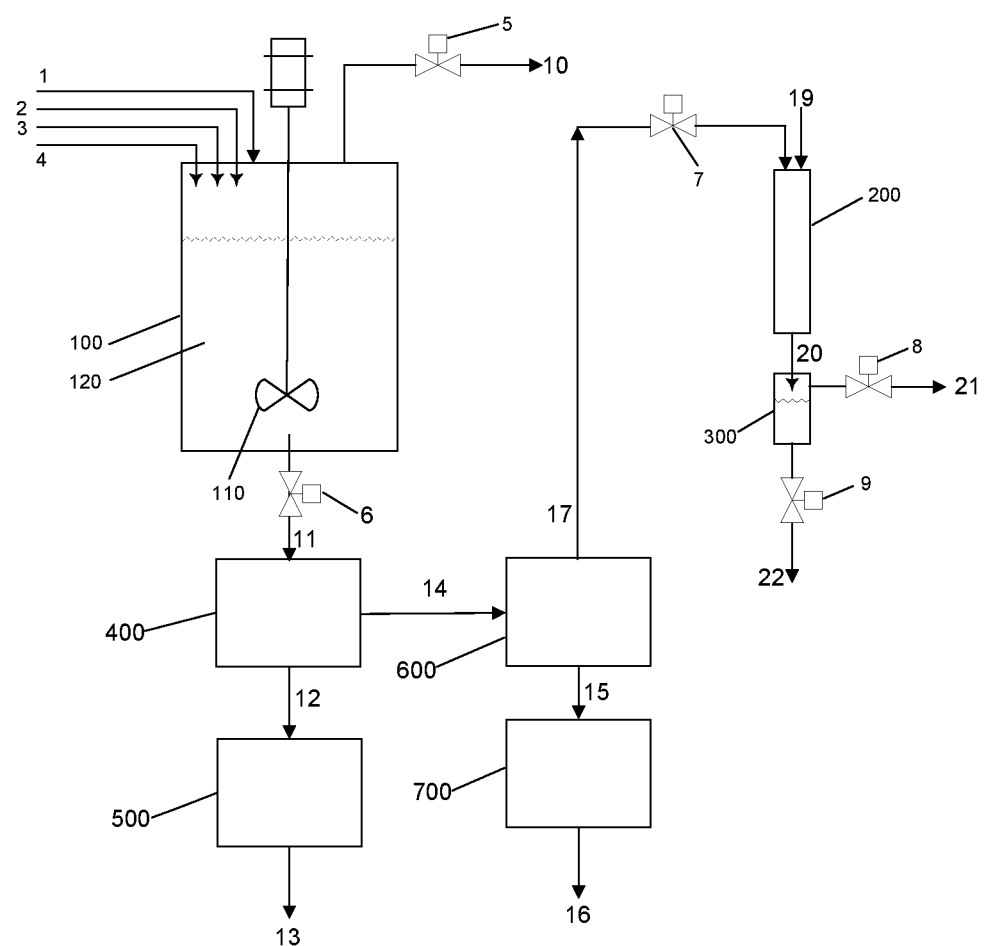
FIG. 2 shows an example process scheme according to an implementation of the disclosed subject matter.

FIG. 2 shows an example process scheme according to an implementation of the disclosed subject matter. An alternate scheme for the use and recovery of catalyst components by the magnetic separation method in the production of glycols from carbohydrate feeds using a catalyst system comprising a heterogeneous hydrogenation catalyst and a homogeneous tungstate retro-Aldol catalyst is shown in FIG. 2. Reactor 100 may be equipped with stirrer 110. The reactor 100 may also be equipped with automatic controls for the control of reactor temperature, back-pressure, liquid holdup level, and stirrer speed. The feed line 1 may be equipped with a gas flowmeter and may be used to provide a continuous flow of hydrogen gas into the reactor 100. Each of the feed lines 2 to 4, may be used to send liquid or slurry streams into the reactor, and may be equipped with a pump and a mass flow meter. These lines 2-4 may be used to continuously add the carbohydrate feed (e.g., glucose solution or slurry of starch in water), solution of sodium meta-tungstate retro-Aldol catalyst, and optionally an alcoholic solvent into the reaction medium 120. Optionally, the carbohydrate feed and the tungstate retro-Aldol catalyst may be combined into a single liquid feed stream. One of the feed lines 2 to 4 may be used to continuously add the heterogeneous hydrogenation catalyst as slurry in water. The excess gas present in the reactor 100 may be vented by the use of the back-pressure control valve 5. The vent gas may be vented via stream 10.

Continuing with reference to FIG. 2, the liquid phase from the reactor 100, comprising the glycols product and the catalyst components, may be continuously removed using the liquid level control valve 6 and sent to the magnetic separation vessel 400 via line 11. The hydrogenation catalyst may be magnetically separated in vessel 400. The magnetically active materials comprising the hydrogenation catalyst may be sent to the storage vessel 500 via line 12. The hydrogenation catalyst may be removed from vessel 500 via line 13 for further conditioning or a direct recycle back into the glycols production in reactor 100. The liquid stream resulting from the magnetic separation in vessel 400, still containing the suspended particles of the W oxides, may be passed to vessel 600 via line 14. The solids may be separated from the liquid in vessel 600, removed via line 15, and sent to storage vessel 700. The solids may be removed from vessel 700, via line 16, for a catalyst reactivation step before recycling to the glycols production in reactor 100.

Also shown in FIG. 2, the liquid product stream from vessel 600 may be sent to reactor 200 via line 17 using the liquid flow control valve 7. The gas feed line 19 may be used to provide hydrogen gas for the reactor 200. Line 20 may be an in-line product cooler to cool down the product mixture. The gas-liquid product effluent passing through line 20 may be set up to flow into a gas/liquid separator vessel 300. Valve 8 may be used to control the back-pressure in vessel 300 and valve 9 may be used to control the liquid level in the vessel. The vent gas may be vented via stream 21 and the product may be removed via stream 22.

Figure 3:
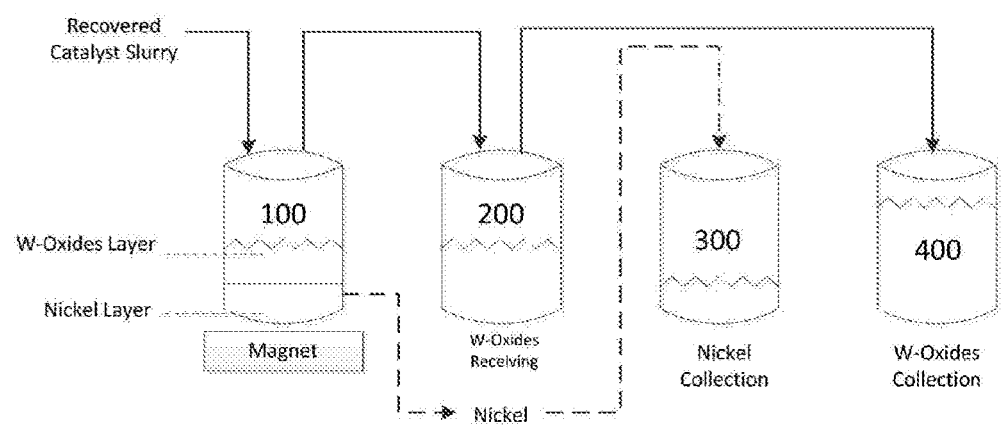
FIG. 3 shows an example process scheme according to an implementation of the disclosed subject matter.

FIG. 3 shows an example process scheme according to an implementation of the disclosed subject matter. An example apparatus that may be used to perform the manual separation of the recovered catalyst mixture comprising Raney®-nickel and the precipitated oxides of tungsten (e.g., W-oxides) is represented in FIG. 3. The recovered catalyst slurry may be poured into vessel 100. A bar magnet may be held under vessel 100. Vessel 200 may be the receiving vessel for the top slurry phase from vessel 100. Vessel 300, which may be the nickel collection vessel, may be used to collect the magnetically separated catalyst phase from vessels 100 and 200. The slurry in vessel 200, consisting mostly of a suspension of W-oxides but still containing some magnetically active nickel catalyst, may be used to perform an additional separation step by holding the bar magnet underneath it. The top slurry phase from vessel 200 may be added to the W-oxides collection vessel 400.

A feature of the presently disclosed subject matter is the ability to run the reaction indefinitely because of the catalyst recovery, magnetic separation, reactivation, and recycle.

As shown in the Examples section provided below, the presently disclosed method for producing ethylene glycol from a carbohydrate feed has numerous advantages over the prior art. The disclosed subject matter allows for magnetic separation of catalyst components for subsequent recycle in the process for producing glycols. An advantage of the disclosed magnetic separation and recycle technique is that it provides a solution to the problem of separating the oxides of tungsten from the hydrogenation catalyst, both of which are present in the reactor as small particles. Another advantage of the disclosed magnetic separation and recycle technique is that it allows the production of the desirable products of EG and PG in high yields and high percentage recovery with a relatively low use of energy, chemical components and complex equipment as compared to prior art processes. This method results in a production of glycols from carbohydrate feeds that makes the overall glycol production process more economical than processes disclosed previously in the industry.

EXAMPLES

Example 1

A continuous stirred tank reactor (CSTR) as shown in FIG. 1 was set up with automatic controls to control the liquid level, reactor back-pressure, temperature, gas and liquid flow rates, and stirrer speed. The volume of the reactor was one liter. A 30.6 gram sample of Raney® nickel catalyst (W. R. Grace, Raney®-Ni 2800) was added to the reactor in the form of slurry and diluted with water to bring the level inside the reactor to 50%. The reactor was pressurized with $N_2$ gas to check for leaks and to remove oxygen from the gas phase. The gas was then replaced with a continuous flow of $H_2$ at a rate of 25 standard liters per hour (SLPH); the back-pressure and stirrer speed were controlled at 1000 PSIG and 1250 RPM respectively. The catalyst was washed with deionized water at a rate of 5 ml per minute, over a period of 3 hours, to remove excess basicity from the catalyst. The temperature was raised to 100° C. and held at conditions for a period of 18 hours to activate the catalyst. After a brief period of experiments to hydrogenate lactic acid under various conditions, the reactor conditions were adjusted to a back-pressure of 1500 PSIG, $H_2$ flow rate of 25 SLPH, temperature of 230° C., and stirrer speed of 1500 RPM (revolutions per minute). An aqueous solution containing 10.0% wt of the glucose sugar feed and 0.30% wt of the sodium meta-tungstate (NaMT) retro-Aldol catalyst was prepared in a 5-gallon feed vessel. The feed solution was added to the reactor at a rate of 4.8 to 4.9 grams per minute. Samples of the reactor effluents, the liquid stream and the vent-gas stream, were analyzed to monitor the progress of the reaction. At the end of 167.6 hours of operation the experiment was terminated.

The reactor was cooled down and flushed with water to remove the glycol products from the spent catalyst, leaving the catalyst as slurry in water. The reactor was de-pressurized, purged with $N_2$ gas, and unbolted. The spent catalyst, a mixture of the nickel catalyst originally added to the reactor and the precipitated oxides of tungsten (W-oxides) in the form of blue-colored slurry in water, was transferred to a collection vessel. Some deposits present on the internal parts of the autoclave vessel were rinsed with water and collected in order to obtain a complete recovery of the solids.

A manual procedure was used to perform the magnetic separation of the nickel and the W-oxides fractions as shown for example in FIG. 3. One-liter size plastic bottles and a neodymium block-magnet were used in this procedure. The magnet had a power of 43.9 pounds-pull. The procedure consisted of the following steps.

1. Transfer the recovered catalyst slurry to the decanting bottle up to the halfway point.
2. Apply the magnet to the outside-bottom of the bottle. Carefully swirl contents to allow nickel to settle and attract to the bottom.
3. While still holding the magnet to outside-bottom of the bottle, carefully decant the W-oxides suspension to the W-oxides receiving bottle.
4. Remove the magnet and then transfer material that is retained in the decanting bottle into the nickel collection bottle.
5. Use water as needed to transfer the contents as slurry.
6. Repeat steps 2 to 5 with the material present in the W-oxides receiving bottle until negligible amounts of magnetically active materials remain in the bottom.
7. Then transfer all of non-magnetic contents into the W-oxides collection bottle.
8. Repeat steps 1 through 7 until all of the slurry recovered from the experiment has been treated and separated into the nickel collection and W-oxides collection bottles.
9. Using the same technique applied in steps 2 to 8, perform additional water washing on the nickel present in the nickel collection bottle to remove any residual W-oxides, until solution is mostly clear.

Each of the nickel and the W-oxides slurry fractions thus collected were filtered using a Buchner funnel and filter paper. The solids were dried and weighed. Samples of the dry solids were analyzed by x-ray fluorescence (XRF), a semi-quantitative analytical technique, to determine the elemental composition of the recovered catalyst components.

Example 2

In this example, slurry of corn starch in water at a concentration of 10% weight was used as feed for the sugars-to-glycols experiment. A slurry feed pump was used to continuously feed the starch solids to the CSTR reactor. The amount of Raney® nickel catalyst added to the reactor was 29.6 grams and the sodium meta-tungstate retro-Aldol catalyst concentration was varied in the 0.29 to 0.38% range. The reaction was terminated at the end of 79.4 hours of operation. The same set of general procedures as in Example 1, namely the CSTR experimental, catalyst recovery, and magnetic separation procedures was used.

Example 3

In this example, slurry of corn starch in water at a concentration of 10% weight was used as feed for the sugars-to-glycols experiment. A slurry feed pump was used to continuously feed the starch solids to the CSTR reactor. The amount of Raney® nickel catalyst added to the reactor was 26.7 grams and the sodium meta-tungstate retro-Aldol catalyst concentration was 0.30%. The reaction was terminated at the end of 18.2 hours of operation. The same set of general procedures as in Example 1, namely the CSTR experimental, catalyst recovery, and magnetic separation procedures was used.

Example 4

In this example, slurry of corn starch in water at a concentration of 10% weight was used as feed for the sugars-to-glycols experiment. A slurry feed pump was used to continuously feed the starch solids to the CSTR reactor. The amount of Raney® nickel catalyst added to the reactor was 26.6 grams and the sodium meta-tungstate retro-Aldol catalyst concentration was varied in the 0.28 to 0.34% range. The reaction was terminated at the end of 166.7 hours of operation. The same set of general procedures as in Example 1, namely the CSTR experimental, catalyst recovery, and magnetic separation procedures was used.

Example 5

In this example, slurry of corn starch in water at a concentration of 10% weight was used as feed for the sugars-to-glycols experiment. A slurry feed pump was used to continuously feed the starch solids to the CSTR reactor. The amount of Raney® nickel catalyst added to the reactor was 28.0 grams and the sodium meta-tungstate retro-Aldol catalyst concentration was varied in the 0.34 to 0.49% range. The reaction was terminated at the end of 131.7 hours of operation. The same set of general procedures as in Example 1, namely the CSTR experimental, catalyst recovery, and magnetic separation procedures was used.

Example 6

In this example, glucose feed at a concentration of 20% weight was used as feed for the sugars-to-glycols experiment. The amount of Raney® nickel catalyst added to the reactor was 28.1 grams and the sodium meta-tungstate retro-Aldol catalyst concentration was varied in the 0.30 to 0.45% range. The reaction was terminated at the end of 146.5 hours of operation. The same set of general procedures as in Example 1, namely the CSTR experimental, catalyst recovery, and magnetic separation procedures was used.

The data from the above Examples 1-6 are shown below. Provided in Table 1 are experimental data consisting of the amount of the nickel catalyst initially added to the reactor, concentrations of the tungstate catalyst and the sugar feed, total experimental run time before spent catalyst was recovered, and the amounts of nickel and tungsten fractions collected using the magnetic separation technique. XRF elemental results of the separated catalyst fractions are provided in Table 2.

tions. High Ni/W ratio in the recovered nickel fraction and high W/Ni ratio in the recovered W-oxide fraction are desirable results. As can be seen from the Examples 1-6 shown, desirable separation of the catalyst components was obtained by the magnetic separation method. As can be seen in Table 2, in Sample 3A, a Ni/W ratio of 75.7 was achieved in Example 3 demonstrating that the nickel catalyst was separated in high purity. As can be seen in Table 2, in Sample 1B, a W/Ni ratio of 16.2 was achieved in Example 1 demonstrating that the oxides of tungsten (W-oxides) was separated in high purity. While the manual method used for the laboratory experiments was relatively easy to carry out, automated equipment may be used in commercial practice to gain further efficiencies, resulting in an even higher purity fractions of both the catalyst components. The nickel and the W-oxide fractions are suitable for reactivation into active forms of the hydrogenation catalyst function and the retro-Aldol function respectively. The reactivated catalysts can be recycled back to the glycols production reactor. The magnetic separation technique, therefore, provides a viable means by which the deactivated catalysts are reused.

One may consider the option of running the glycols production reaction using the catalyst system consisting of a heterogeneous hydrogenation catalyst and soluble tungstate retro-Aldol catalyst under conditions that prevent the for-

TABLE 1

Examples Showing Magnetic Separation of Recovered Solid

| | | Catalyst & Sugar Feed to Reactor | | | Recovered Amounts | |
|---|---|---|---|---|---|---|
| Example | Run Time [Hours] | Fresh Ni Charge [Gram] | NaMT Conc in Feed [Wt %] | Sugar Feed [Wt %] | Ni Fraction [Gram] | W-oxide [Gram] |
| 1 | 167.3 | 30.6 | 0.30 | Glucose [10%] | 34.0 | 86.3 |
| 2 | 79.4 | 29.6 | 0.29-0.38 | Starch [10%] | 33.0 | 14.4 |
| 3 | 18.2 | 26.7 | 0.30 | Starch [10%] | 26.0 | ND |
| 4 | 166.7 | 26.6 | 0.28-0.34 | Starch [10%] | 31.9 | 85.6 |
| 5 | 131.7 | 28.0 | 0.34-0.49 | Starch [10%] | 33.7 | 67.1 |
| 6 | 146.5 | 28.1 | 0.30-0.45 | Glucose [20%] | 41.5 | 137.6 |

NaMT = Sodium Meta-Tungstate;
ND = Not Determined

TABLE 2

Elemental Composition Analysis of Recovered Catalyst Fractions

| | | XRF Semi-Quantitative, % wt* | | | Atom Ratio | | |
|---|---|---|---|---|---|---|---|
| Sample Id | Description | Al | Ni | W | Al/Ni | W/Ni | Ni/W |
| | Fresh Raney-Ni | 5.4 | 69.7 | | 0.17 | 0.00 | |
| 1A | Recov Ni | 3.0 | 66.2 | 13.3 | 0.10 | 0.06 | 15.6 |
| 1B | Recov W-Oxides | 0.4 | 1.3 | 66.0 | 0.70 | 16.2 | 0.06 |
| 2A | Recov Ni | 2.2 | 71.3 | 6.9 | 0.07 | 0.03 | 32.2 |
| 2B | Recov W-Oxides | 3.1 | 8.0 | 70.1 | 0.85 | 2.81 | 0.36 |
| 3A | Recov Ni | 3.0 | 65.9 | 2.7 | 0.10 | 0.01 | 75.7 |
| 4A | Recov Ni | 1.9 | 56.8 | 23.3 | 0.07 | 0.13 | 7.64 |
| 4B | Recov W-Oxides | 0.4 | 6.6 | 71.4 | 0.14 | 3.43 | 0.29 |
| 5A | Recov Ni | 1.5 | 69.2 | 11.6 | 0.05 | 0.05 | 18.6 |
| 5B | Recov W-Oxides | 0.6 | 2.0 | 74.9 | 0.62 | 11.9 | 0.08 |
| 6A | Recov Ni | 1.8 | 41.5 | 33.0 | 0.10 | 0.25 | 3.95 |
| 6B | Recov W-Oxides | 0.5 | 14.4 | 70.3 | 0.08 | 1.56 | 0.64 |

*Calculated based on the assumption that the elements were in their common oxide forms;
XRF = X-Ray Fluorescence. Samples in the above Table 2 are identified by the Example numbers given in Table 1 - samples 1A and 1B are the magnetically separated nickel and W-oxide fractions respectively from Example 1, and so on.

The W/Ni and the Ni/W atomic ratios shown in Table 2 are indicators of the purity of the separated catalyst fracmation of the insoluble W-oxides, thus prolonging the life of the catalyst system and possibly eliminating the need to recycle the catalysts. It has been determined that, in general, the glycol yields are poor under these conditions. In order to make the process economically viable, it is necessary to produce the glycols in relatively high EG/PG combined yields of at least 75% by weight. In general, the catalyst system is less stable under high yield conditions, thus requiring a method for the separation of the catalysts components before they can be reactivated into active forms suitable for their recycle. Overall, the magnetic separation method provides a means for achieving the desirable economic targets.

The foregoing description, for purpose of explanation, has been described with reference to specific embodiments. However, the illustrative discussions above are not intended to be exhaustive or to limit embodiments of the disclosed subject matter to the precise forms disclosed. Many modifications and variations are possible in view of the above teachings. The embodiments were chosen and described in order to explain the principles of embodiments of the disclosed subject matter and their practical applications, to thereby enable others skilled in the art to utilize those embodiments as well as various embodiments with various modifications as may be suited to the particular use contemplated.

That which is claimed is:

1. A process for producing ethylene glycol from a carbohydrate feed comprising:
   a) contacting, in a reactor under hydrogenation conditions, the carbohydrate feed with a bi-functional catalyst system comprising:
      1) a heterogeneous hydrogenation catalyst comprising a magnetically active metal, and
      2) a soluble retro-Aldol catalyst comprising tungstate;
   b) obtaining a liquid effluent stream, from the reactor, comprising hydrogenation catalyst particles and tungsten oxide precipitate particles;
   c) magnetically separating the hydrogenation catalyst particles from the tungsten oxide precipitate particles in the liquid effluent stream using a magnet in a separation vessel, wherein the separated hydrogenation catalyst particles are retained in a separation zone in the separation vessel;
   d) removing the separated hydrogenation catalyst particles from the separation zone,
   e) obtaining a liquid product stream, from the separation vessel, wherein the liquid product stream comprises the tungsten oxide precipitate particles and ethylene glycol.

2. The method of claim 1, wherein the separated hydrogenation catalyst particles from step (d) are combined with at least a portion of the liquid product stream to form a slurry that is recycled back to step (a).

3. The method of claim 1, wherein the magnetically active metal is at least one selected from the group consisting of: nickel, cobalt, iron, rare earth metals, and combinations thereof.

4. The method of claim 1, wherein the magnet used in step (c) is selected based on at least one property selected from the group consisting of: magnetic power of the magnet, particle size of the hydrogenation catalyst particles, velocity of the liquid effluent from the reactor, and the magnetic power of the magnetically active metal of the hydrogenation catalyst.

5. The method of claim 1, wherein the separation vessel is a drum separator.

6. The method of claim 1, wherein the heterogeneous hydrogenation catalyst is a Raney-type catalyst.

7. The method of claim 1, wherein the heterogeneous hydrogenation catalyst is a hydrogenation catalyst supported on a hydrothermally stable support.

8. The method of claim 6, wherein the heterogeneous hydrogenation catalyst comprises at least one selected from the group consisting of: Raney-Ni, Raney-Co, Raney-Cu, Raney-Ru, Raney-Ni, Cu, Co, Ru, and any hydrogenation catalyst in nano-particle metal form.

9. The method of claim 8, wherein the heterogeneous hydrogenation catalyst is further promoted with one or more selected from the group consisting of: Fe, Cr, Mn, Mo, W, Re, Rh, Pd, Ag, Au, Pt, Ir, and La.

10. The method of claim 1, wherein the tungstate in the soluble retro-Aldol catalyst is at least one selected from the group consisting of: sodium meta-tungstate, ammonium meta-tungstate, ammonium tungstate, sodium poly-tungstate, tungstic acid, alkali- and alkaline-earth metal tungstates, sodium phospho-tungstate, phospho-tungstic acid, alkali- and alkaline-earth metal phospho-tungstates, alkali- and alkaline-earth metal molybdates, alkali- and alkaline-earth metal phospho-molybdates, phospho-molybdic acid, heteropoly acids, mixed tungstates and molybdates, niobic acid, silicotungstic acid, alkali- and alkaline-earth metal niobates.

* * * * *